United States Patent [19]

Thornton et al.

[11] Patent Number: 5,678,567
[45] Date of Patent: Oct. 21, 1997

[54] APPARATUS FOR ADJUSTING A DENTAL DEVICE

[76] Inventors: W. Keith Thornton, 5524 Edlen, Dallas, Dallas County, Tex. 75220; Andrew Orr Jamieson, 9426 Hillview Dr., Dallas, Dallas County, Tex. 75231

[21] Appl. No.: 501,437

[22] Filed: Sep. 18, 1995

Related U.S. Application Data

[63] Continuation of Ser. No. 435,277, May 5, 1995, which is a continuation of Ser. No. 218,719, Mar. 25, 1994, abandoned.

[51] Int. Cl.$^6$ ..................................................... A61F 5/56
[52] U.S. Cl. ............................................. 128/848; 128/861
[58] Field of Search .................................... 128/846, 848, 128/859–862; 433/68–72, 214

[56] References Cited

U.S. PATENT DOCUMENTS

| | | |
|---|---|---|
| 746,869 | 12/1903 | Moulton . |
| 1,076,534 | 10/1913 | Wallen . |
| 1,146,264 | 7/1915 | Kelly . |
| 1,649,664 | 11/1927 | Carter . |
| 1,674,336 | 6/1928 | King . |
| 2,171,695 | 9/1939 | Harper . |
| 2,424,533 | 7/1947 | Faires ........................... 128/136 |
| 2,521,039 | 9/1950 | Carpenter ................... 128/136 |
| 2,531,222 | 11/1950 | Kesling ........................... 32/14 |
| 2,590,118 | 3/1952 | Oddo, Jr. ....................... 128/136 |
| 2,833,278 | 5/1958 | Ross ............................... 128/136 |
| 2,882,893 | 4/1959 | Godfroy ........................ 128/136 |
| 3,107,668 | 10/1963 | Thompson ..................... 128/136 |

(List continued on next page.)

FOREIGN PATENT DOCUMENTS

| | | |
|---|---|---|
| 0312368 | 4/1989 | European Pat. Off. . |
| 0359135 | 3/1990 | European Pat. Off. . |
| 2320501 | 11/1974 | Germany . |
| 1569129 | 6/1980 | United Kingdom . |

OTHER PUBLICATIONS

Brochure from Professional Positioners (no date).

*Primary Examiner*—Michael A. Brown
*Attorney, Agent, or Firm*—Baker & Botts, L.L.P.

[57] ABSTRACT

A method and apparatus for fitting a dental device are provided in which an upper arch (12) receives a drive mechanism (16). Drive mechanism (16) is controlled by a controller (32). The drive mechanism (16) allows for translational adjustment of a post (18). Post (18) contacts a lower arch (14), thereby causing a user's lower jaw to extend forward. The post (18) is adjusted for maximum effectiveness in reducing snoring while maintaining comfort. The position of the post (18) is then recorded and a permanent dental device is made with a post in a corresponding position.

9 Claims, 2 Drawing Sheets

U.S. PATENT DOCUMENTS

| | | | |
|---|---|---|---|
| 3,124,129 | 3/1964 | Grossberg | 128/136 |
| 3,321,832 | 5/1967 | Weisberg | 32/32 |
| 3,434,470 | 3/1969 | Strickland | 128/136 |
| 3,457,916 | 7/1969 | Wolicki | 128/136 |
| 3,513,838 | 5/1970 | Foderick et al. | 128/861 |
| 3,854,208 | 12/1974 | Arant | 433/73 |
| 3,864,832 | 2/1975 | Carlson et al. | 128/136 |
| 3,871,370 | 3/1975 | McDonald | 128/136 |
| 4,016,650 | 4/1977 | Leusner et al. | 32/17 |
| 4,026,024 | 5/1977 | Tradowsky | 32/19 |
| 4,114,614 | 9/1978 | Kesling | 128/136 |
| 4,182,312 | 1/1980 | Mushabac | 433/68 |
| 4,227,877 | 10/1980 | Tureaud et al. | 433/37 |
| 4,304,227 | 12/1981 | Samelson | 128/136 |
| 4,376,628 | 3/1983 | Aardse | 433/80 |
| 4,439,147 | 3/1984 | Magill et al. | 433/3 |
| 4,495,945 | 1/1985 | Leigner | 128/200.26 |
| 4,505,672 | 3/1985 | Kurz | 433/6 |
| 4,553,549 | 11/1985 | Pope et al. | 128/421 |
| 4,568,280 | 2/1986 | Ahlin | 433/6 |
| 4,569,342 | 2/1986 | von Nostitz | 128/136 |
| 4,593,686 | 6/1986 | Lloyd et al. | 128/136 |
| 4,602,905 | 7/1986 | O'Keefe, III | 433/41 |
| 4,639,220 | 1/1987 | Nara et al. | 433/69 |
| 4,773,853 | 9/1988 | Kussick | 433/6 |
| 4,799,500 | 1/1989 | Newbury | 128/859 |
| 4,862,903 | 9/1989 | Campbell | 128/861 |
| 4,901,737 | 2/1990 | Toone | 128/848 |
| 4,932,867 | 6/1990 | Ueno | 433/69 |
| 4,955,393 | 9/1990 | Adell | 128/859 |
| 5,003,994 | 4/1991 | Cook | 128/848 |
| 5,018,533 | 5/1991 | Hawkins | 128/848 |
| 5,028,232 | 7/1991 | Snow | 433/24 |
| 5,042,506 | 8/1991 | Liberati | 128/848 |
| 5,056,534 | 10/1991 | Wright | 128/848 |
| 5,078,600 | 1/1992 | Austin | 433/73 |
| 5,092,346 | 3/1992 | Hays et al. | 128/848 |
| 5,103,838 | 4/1992 | Yousif | 128/859 |
| 5,117,816 | 6/1992 | Shapiro et al. | 128/200.24 |
| 5,154,609 | 10/1992 | George | 433/68 |
| 5,183,057 | 2/1993 | Syrop et al. | 128/845 |
| 5,188,529 | 2/1993 | Luth | 433/68 |
| 5,267,862 | 12/1993 | Parker | 433/215 |
| 5,277,202 | 1/1994 | Hays | 128/848 |
| 5,313,960 | 5/1994 | Tomasi | 128/848 |

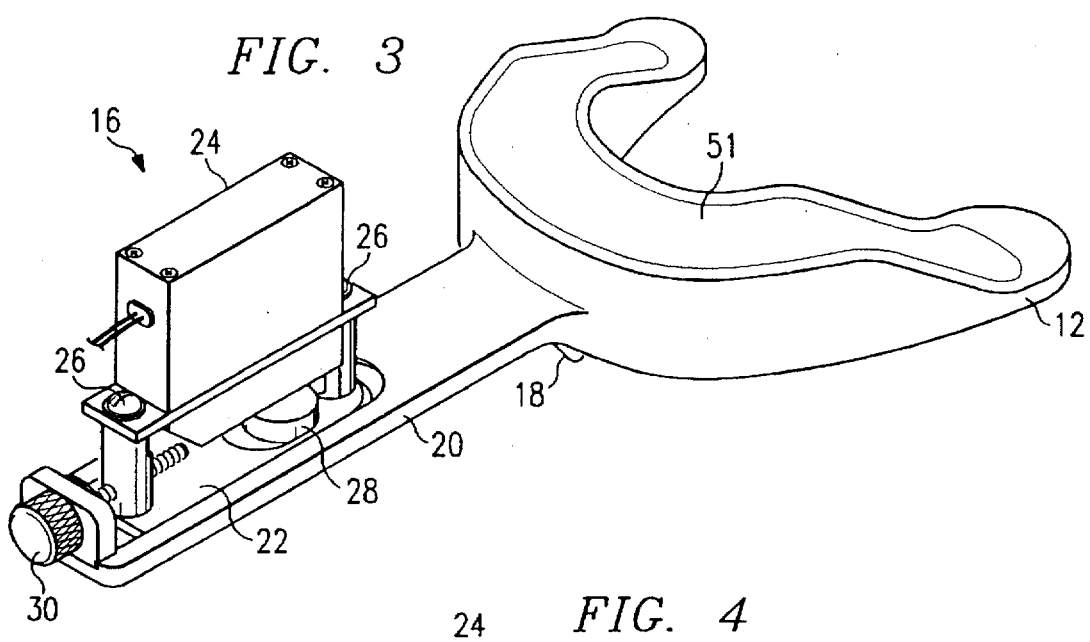
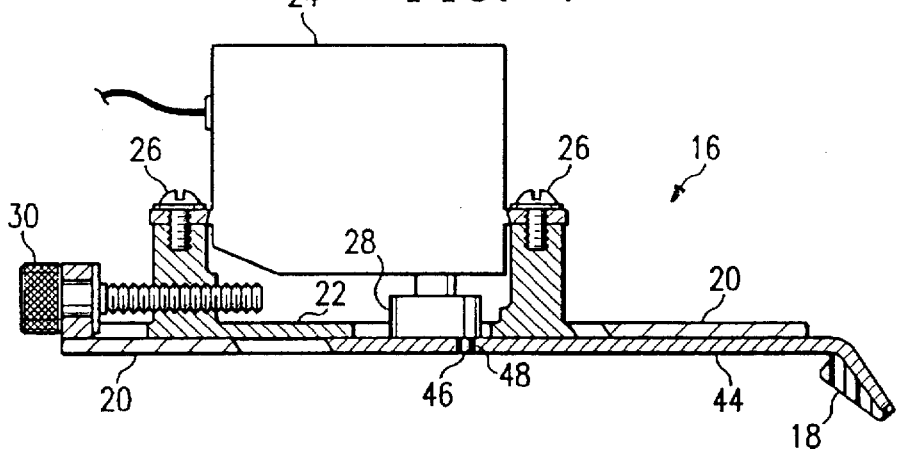
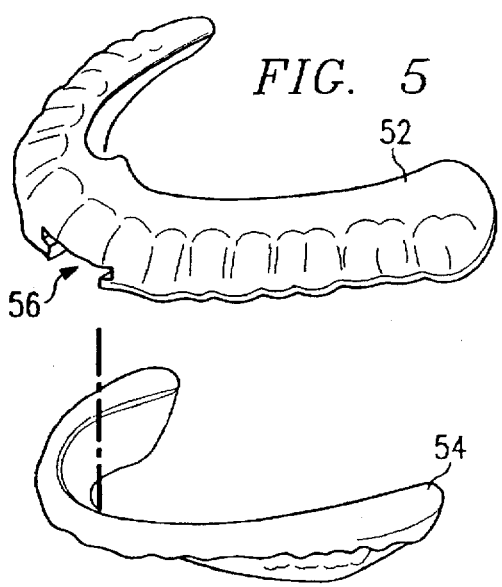
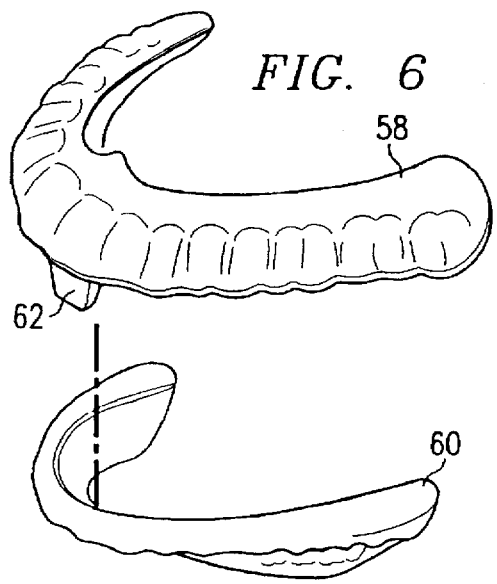

APPARATUS FOR ADJUSTING A DENTAL DEVICE

This application is a continuation application of U.S. application Ser. No. 08/435,277, filed May 5, 1995 and entitled "A Method of Fitting a Dental Device," (As Amended) by W. Keith Thornton and Andrew O. Jamieson, now pending, which is a continuation application of U.S. application Ser. No. 08/218,719, filed Mar. 25, 1994 and entitled "Method and Apparatus for Adjusting a Dental Device," by W. Keith Thornton and Andrew O. Jamieson, now abandoned.

CROSS-REFERENCES TO RELATED APPLICATIONS

This application is related to U.S. patent application Ser. No. 08/129,598, filed Sep. 29, 1993, and entitled APPARATUS FOR PREVENTION OF SNORING AND IMPROVED BREATHING DURING SLEEP.

TECHNICAL FIELD OF THE INVENTION

This invention relates generally to medical devices, and more particularly to a method and apparatus for adjusting a dental device.

BACKGROUND OF THE INVENTION

Snoring is a problem that plagues millions of people, and can be a significant problem, as it often diminishes the quality of sleep of the snorer. Moreover, snoring may be a symptom of a more serious sleep apnea problem.

A technique that has been used to reduce or eliminate snoring involves extending the lower jaw forward, so as to open the breathing passageway. For example, U.S. Pat. Nos. 5,117,816, 5,003,994, and 5,092,346 disclose devices that extend the lower jaw forward.

Extending the lower jaw forward will be successful in preventing or reducing snoring only if the lower jaw is extended far enough forward to open the air passageway. However, the lower jaw must not be extended so far forward that it is uncomfortable, as the snorer would not use a device with that result.

Therefore, a need has arisen for a method and apparatus for adjusting and fitting a dental device that maximizes the opening of the air passageway while maintaining comfort.

SUMMARY OF THE INVENTION

In accordance with the teachings of the present invention, a method and apparatus for adjusting and fitting a dental device are provided which substantially eliminate or reduce disadvantages and problems associated with prior art dental devices.

In particular, a dental device is provided which includes an upper arch. A post extends downward from the upper arch and is coupled to a drive mechanism. The drive mechanism is operable to translationally adjust the post. The adjustment of the post can be performed by a dental professional to insure effective reduction of snoring while maintaining comfort. The position of the post is then recorded and a permanent dental device can be made with a post in a corresponding position.

In a particular embodiment, the drive mechanism includes a motor and a stage coupled to the motor and to the post. The motor operates to translationally adjust the stage. A controller may also be provided for controlling the motor, with the controller including a display of the position of the post.

Furthermore, a method of fitting dental devices provided in which an upper arch is inserted into the user's mouth, the arch having a downwardly extending post. While the arch is in the user's mouth, the post is adjusted to locate the user's jaw in a particular location.

In addition, the position of the post at which the user's jaw is located in the particular position can be recorded, and then a permanent dental device can be fabricated, based on the recorded post position, such that the permanent dental device locates the user's lower jaw in the particular location.

An important technical advantage of the present invention is the fact that a dental device can be adjusted and fitted such that the lower jaw will be maintained in an optimal position for reducing or preventing snoring and for maintaining comfort for the user.

BRIEF DESCRIPTION OF THE DRAWINGS

For a more complete understanding of the present invention and its advantages, reference is now made to the following description taken in conjunction with the accompanying drawings in which like references numbers indicate like features and wherein:

FIG. 3 illustrates another embodiment of a dental device and drive mechanism according to the teachings of the present invention;

FIG. 4 illustrates a sectional view of a drive mechanism according to the teachings of the present invention;

FIG. 5 illustrates an alternative embodiment with a custom-fitted mouthpiece according to the teachings of the present invention; and FIG. 6 illustrates a permanent dental device constructed according to the teachings of the present invention.

DETAILED DESCRIPTION OF THE INVENTION

Figure 1:
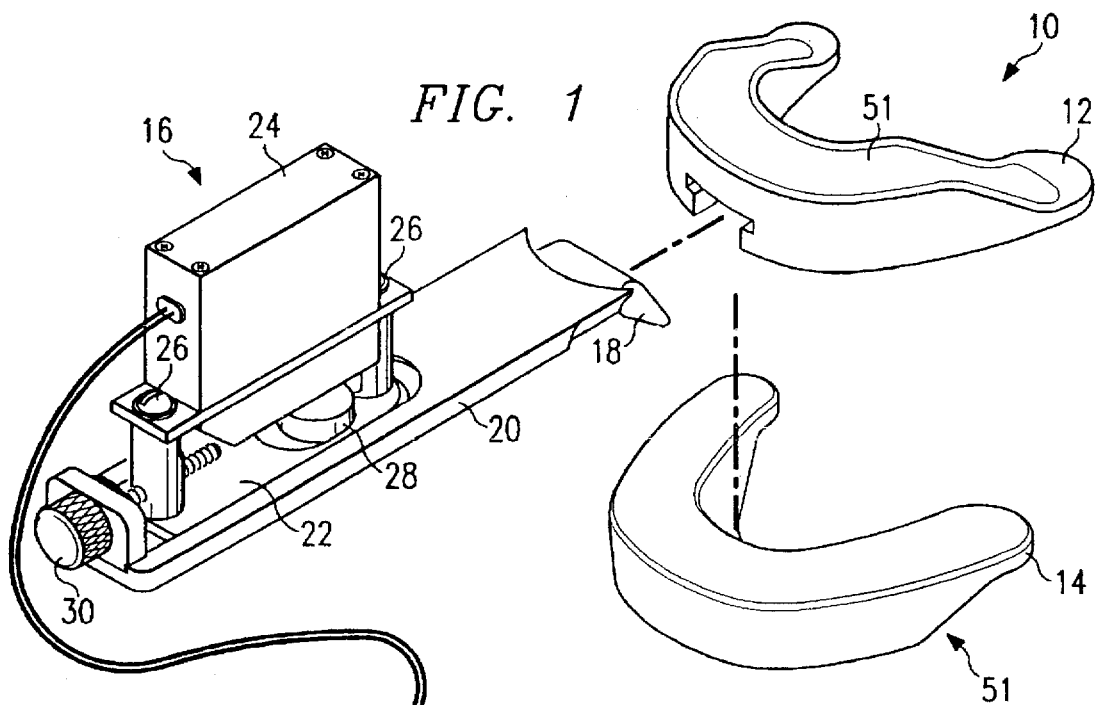
FIG. 1 illustrates an isometric view of a dental device and drive mechanism according to the teachings of the present invention.

FIG. 1 illustrates a dental device 10 according to the present invention. As shown in FIG. 1, an upper arch 12 and a lower arch 14 are provided. The upper arch 12 is inserted in a user's mouth, with the upper arch of teeth fitting in upper arch 12. Likewise, lower arch 14 is inserted in the user's mouth, with the lower arch of teeth fitting in lower arch 14. Upper arch 12 may fit over all or only some of the user's upper teeth. Likewise, lower arch 14 may fit over all or only some of the user's lower teeth.

A drive mechanism 16 slides into upper arch 12, and includes a downwardly extending post 18. The downwardly extending post 18 contacts the lower arch 14, causing the user's lower jaw to extend forward. In a clinical setting, a dental professional uses drive mechanism 16 to translationally adjust post 18 such that the lower jaw of the user is adjusted. By adjusting the position of lower jaw 14, the dental professional can determine the optimal position for the post 18.

For example, a dental professional can adjust the position of post 18 so that the user's lower jaw is extended to the furthest position forward that is still comfortable. Once this position is reached, the position of the post 18 is recorded and a permanent dental device is manufactured with a post positioned according to the results of the clinical test. Similarly, the device shown in FIG. 1 can be used on a sleeping patient, with the post 18 adjusted until snoring stops.

As shown in FIG. 1, drive mechanism 16 includes a platform 20. Sliding within platform 20 is a stage 22 on which is mounted a motor 24. Motor 24 may be a motor such as an ACE R/C import special 380 motor. Motor 24 is mounted to stage 22 with screws 26. The motor's circular shaft 28 allows for translational adjustment of post 18.

Zero-setting screw 30 is used to adjust the location of post 18 to a known location before adjusting it within the user's mouth. In operation, zero-setting screw 30 moves the location of stage 22 and motor 24, and therefore post 18, to a known zero position. Then, when the post 18 is adjusted in the user's mouth through the use of motor 24, the relative distance that post 18 has moved can be measured. Other zero-setting mechanisms may also be used without departing from the intended scope of the present invention.

A control unit 32 is used to drive motor 24. Control unit 32 includes a dial 34 for turning the motor. A display 36 displays the distance that the post 18 has traveled as dial 34 is turned. Motor 24 is bi-directional, and thus dial 34 allows for forward and backward positioning of post 18. Once the post 18 is in the zero position, zero button 38 may be depressed to reset the display 36.

Figure 2:
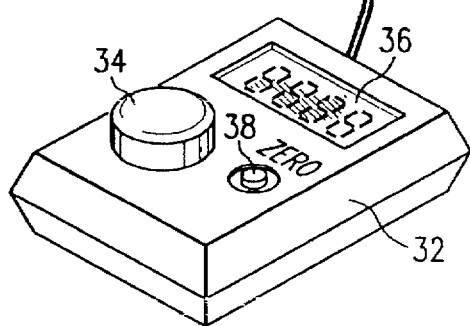
FIG. 2 illustrates a bottom isometric view of a dental device and drive mechanism according to the teachings of the present invention.
Figure 2:
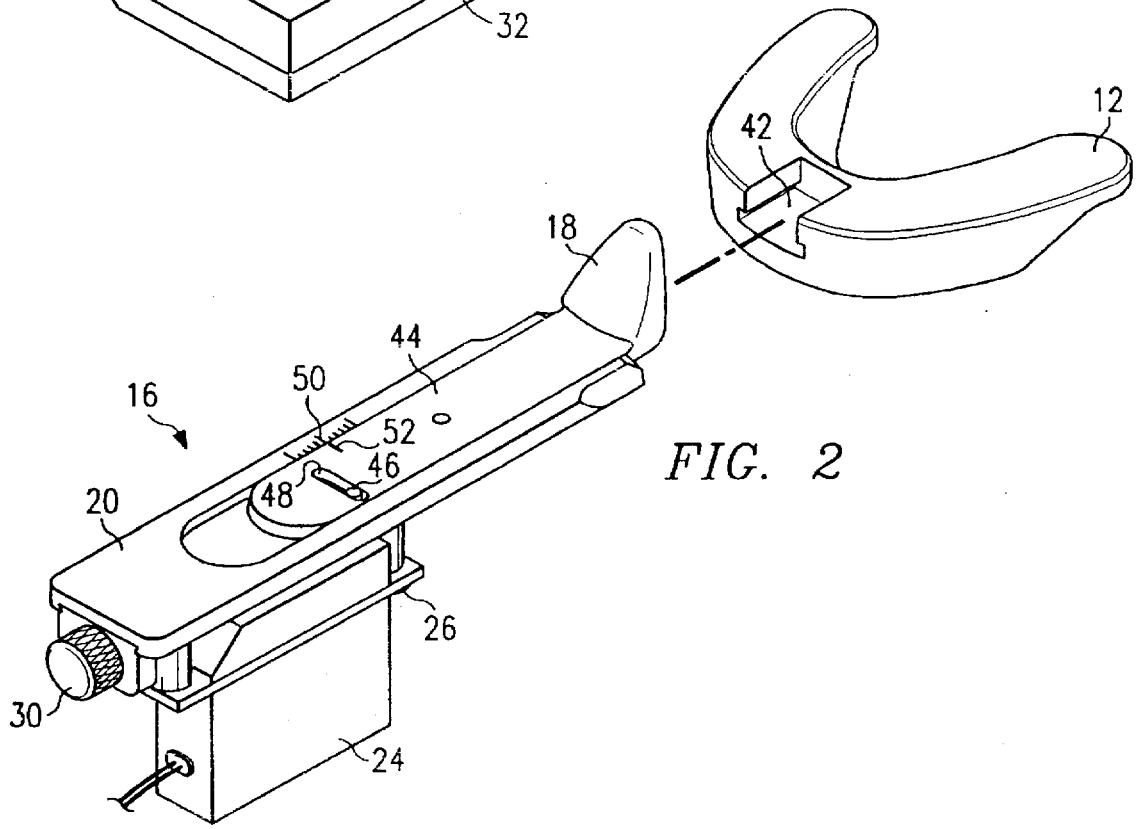

FIG. 2 illustrates a bottom view of upper arch 12 and drive mechanism 16. As shown in FIG. 2, the platform 20 is inserted into slot 42 of upper arch 12. Once inserted and in the user's mouth, the motor 24 is driven so as to translationally adjust post 18. As shown in FIG. 2, post 18 is connected to a stage 44. Stage 44 is coupled to pin 46 through slot 48. The pin 46 resides on the perimeter of circular shaft 28 of motor 24.

In operation, the pin 46 rotates on the perimeter of circular shaft 28. As pin 46 rotates, it forces stage 44, and therefore post 18, to move in and out. This movement can be minutely controlled by controller 32. As discussed above, a dental professional can carefully adjust the position of post 18 to the most effective yet comfortable position. The relative movement of post 18 can be measured through use of scale 50. Scale 50 may be incremented, for example, in millimeters. The line 52 on stage 44 can be used, with scale 50, to determine how far the post 18 is moved. Similarly, as discussed above, the display 36 of controller 32 may be used to determine the position of post 18.

FIG. 3 illustrates an alternative embodiment of the present invention in which the upper arch 12 and the drive mechanism 16 are integrally formed, and thus drive mechanism 16 cannot be removed from arch 12.

FIG. 4 illustrates a sectional view of drive mechanism 16. As shown in FIG. 4, stages 22 and 44 slide within platform 20. The stages 22 and 44 are bevelled so as to dovetail within stage 22. Stage 22 slides in response to zero-setting screw 30. By adjusting zero-setting screw 30, stage 22 and motor 24 are translationally moved. Furthermore, this translational movement of stage 22 moves stage 44 and post 18, since pin 46 resides within slot 48 of stage 44. Once the zero-setting has been performed, then the motor 24 can be used to adjust the post 18. As discussed above, as circular shaft 28 turns, pin 46 causes stage 44, and therefore post 18, to move backwards and forwards.

As shown in FIG. 4, the post 18 is bonded to stage 44. In a preferred embodiment, the shape of post 18 conforms to the shape of the post that will be used in the permanent device fabricated based on the positioning performed with drive mechanism 16. The material of post 18 shown in FIG. 4 may be any material suitable for dental usage.

The platform 20, stage 22, stage 44, and zero-setting screw 30 may be made of a metal, such as aluminum or stainless steel. Other materials may also be used without departing from the intended scope of the present invention.

The particular drive mechanism shown and discussed above is exemplary only. Other mechanisms may also be used to adjust the post 18 without departing from the teachings herein.

The upper and lower arches 12 and 14 shown in FIG. 1 may be made from any material suitable for dental uses, such as methylmethacrylate or a polycarbonate resin thermo plastic such as that sold under the registered trademark LEXAN. Such materials are known to those familiar with dental mouthpieces, and other materials may be used without departing from the intended scope of the present invention.

As shown in FIG. 1, upper and lower arches 12 and 14 may include a deformable material 51. Deformable material 51 is bonded to the upper and lower arches 12 and 14 and used for forming a mold of the user's teeth for proper fitting. A suitable material for deformable material 51 is the ethylene-vinyl acetate copolymer resin sold under the registered trademark ELVAX. Any other suitable deformable materials may also be used. Typically, with a material such as ELVAX, the material 51 is heated to a temperature of about 150 degrees Fahrenheit, through a microwave oven or by heating in hot water, for example, so as to place the material 51 in its deformable state. A user then inserts the arches and bites down, thereby deforming the material 51 into the shape of the user's teeth. The arches are then removed and allowed to cool, thereby setting the material into a mold of the user's teeth.

FIG. 5 illustrates an alternative embodiment of the present invention in which a customized dental mold of the user's teeth are first made before using drive mechanism 16. As shown in FIG. 5, upper arch 52 and lower arch 54 are provided, which are custom made to the user's teeth. Such molds may be made by dental professionals. Upper arch 52 includes a slot 56 in which drive mechanism 16 is inserted. The techniques used to locate the appropriate position for post 18 are then performed as discussed above in connection with FIG. 1-4.

The present invention may also be used without lower arches. With such embodiments, the post 18 causes the lower jaw to extend by coming into contact with the bottom teeth and gums.

Once the optimal position of post 18 has been located, a permanent dental device is fabricated with a post 18 permanently positioned so as to locate the lower jaw in the position determined through use of drive mechanism 16. The post is positioned, in the permanent device, based on the measurements taken when adjusting post 18. FIG. 6 illustrates such a permanent dental device. As shown in FIG. 6, upper arch 58 and lower arch 60 are formed. Furthermore, upper arch 58 is formed with post 62 positioned according to the results of the fitting performed with drive mechanism 16. The particular embodiment shown in FIG. 6 shows a custom made mold of the user's teeth. It should be understood that other molds, similar to those shown in FIG. 1, with a deformable material, may also be used. With such an embodiment, the post is permanently affixed in the appropriate location, and the user can then self-customize the upper and lower arches.

The lower arch 54 shown in FIG. 5 need not be remade for the final device shown in FIG. 6. Thus, for the customized embodiment, only one bottom arch need be made. Furthermore, the customized bottom arch shown in FIGS. 5 and 6 may be made and used in connection with the embodiments shown in FIGS. 1, 2 and 3.

As another use for the drive mechanism 16, and particularly in connection with the embodiment shown in FIG. 3, the drive mechanism may remain inserted with the upper arch while the user sleeps in his day-to-day life. If he begins to snore, his companion may, through controller 32, adjust the position of the post 18 so as to reduce or prevent snoring.

In summary, a method and apparatus for adjusting and fitting a dental device for preventing snoring are provided in which a downwardly extending post may be adjusted for maximum effectiveness and comfort. Once this position of maximum comfort and effectiveness is determined, it is measured and a more permanent dental device is fabricated with a downwardly extending post located according to the measured position.

Although the present invention and its advantages have been described in detail, it should be understood the various changes, substitutions, and alterations can be made herein without departing from the spirit and scope of the invention as defined by the appended claims.

What is claimed is:

1. A dental device, comprising:
   an upper arch;
   a post extending downward from the upper arch; and
   a drive mechanism coupled to said post and operable to translationally adjust the post, the drive mechanism comprising:
   a motor; and
   a stage coupled to the motor and to the post, the motor operable to translationally adjust the stage.

2. The device of claim 1, further comprising a controller for controlling the motor, the controller including a display of the position of the post.

3. The device of claim 1, wherein the drive mechanism further comprises a zero-setting mechanism operable to translationally adjust the post to a known position.

4. The device of claim 3, wherein the zero-setting mechanism comprises a screw operable to translationally adjust the post to a known position.

5. The device of claim 1, wherein the drive mechanism further comprises a scale operable to measure the relative position of the post.

6. The device of claim 1, further comprising a platform, the post being slidably engaged with the platform.

7. The device of claim 6, wherein the platform is formed integrally with the upper arch.

8. The device of claim 6, wherein the platform slidably engages with the upper arch.

9. The device of claim 1, further comprising a lower arch, the post contacting the lower arch to cause a user's lower jaw to extend forward relative to the user.

* * * * *